United States Patent [19]

Mark, Jr.

[11] Patent Number: 4,631,533

[45] Date of Patent: Dec. 23, 1986

[54] DISPLAY OF EDDY CURRENT DETECTOR DATA

[75] Inventor: Richard H. Mark, Jr., Pitcairn, Pa.

[73] Assignee: Westinghouse Electric Corp., Pittsburgh, Pa.

[21] Appl. No.: 621,002

[22] Filed: Jun. 15, 1984

[51] Int. Cl.$^4$ ............................................. G09G 1/06
[52] U.S. Cl. .................................. 340/721; 340/743; 324/232; 324/233
[58] Field of Search ............... 340/709, 721, 722, 723, 340/743, 754, 720, 701; 324/232, 233

[56] References Cited

U.S. PATENT DOCUMENTS

| | | | |
|---|---|---|---|
| 3,406,387 | 10/1968 | Werme | 340/722 X |
| 3,476,974 | 11/1969 | Turnage, Jr. et al. | 340/743 X |
| 3,596,284 | 7/1971 | Zaphiropoulos | . |
| 3,599,033 | 8/1971 | Stettiner | 340/722 X |
| 3,895,290 | 7/1975 | Audenard et al. | . |
| 4,210,917 | 7/1980 | Lane, III | . |
| 4,237,419 | 12/1980 | Tornblom et al. | 324/232 X |
| 4,303,885 | 12/1981 | Davis et al. | 324/232 X |
| 4,328,491 | 5/1982 | Demetrescu et al. | 340/723 X |
| 4,346,378 | 8/1982 | Shanks | 340/754 |
| 4,405,920 | 9/1983 | Weisstein | 340/723 X |
| 4,467,281 | 8/1984 | Davis et al. | 324/233 X |
| 4,498,080 | 2/1985 | Culver | 340/723 X |
| 4,510,571 | 4/1985 | Dagostino et al. | 340/723 X |
| 4,550,316 | 10/1985 | Whetstone et al. | 340/709 X |
| 4,586,036 | 4/1986 | Thomson et al. | 340/720 |

*Primary Examiner*—Gerald L. Brigance
*Assistant Examiner*—Vincent P. Kovalick
*Attorney, Agent, or Firm*—Daniel C. Abeles

[57] ABSTRACT

A method and apparatus for producing a display of eddy current test data from signals produced by an eddy current detector which is supplied with an alternating current signal composed of alternating currents at several different frequencies, the detector signals including a respective signal associated with each current frequency and varying in amplitude and in phase relative to its associated alternating current as the detector is displaced relative to a test body. For each detector signal, a data signal representing the detector signal component in phase with the associated alternating current and a data signal representing the detector signal component in quadrature with the associated alternating current are generated, a representation of each data signal is stored, and the representation of each data signal is supplied to a display device for producing a first display composed of visible representations of all data signals along parallel axis, with each axis being associated with a respective data signal and being representative of the movement of the detector relative to the test body. When desired, end points of a visible representation of a data signal along the axis associated with that representation are selected and a second display representing the ratio of the value of that data signal to the value of the data signal generated from the same detector signal, for signal values between the selected end points, is produced.

9 Claims, 2 Drawing Figures

DISPLAY OF EDDY CURRENT DETECTOR DATA

BACKGROUND OF THE INVENTION

The present invention relates to the display of data derived from an eddy current detector, particularly in connection with the testing of metal parts, such as steam generator tubes.

Known eddy current detectors include two coils mounted in adjacent arms of a bridge. An alternating current is passed through the bridge to generate an electromagnetic field. This field will be influenced by an adjacent metal body to vary the impedance of one or both coils, thereby creating an unbalance voltage in the bridge, which voltage is the difference between the voltages across the two coils. Thus, the waveform of the unbalance voltage is constituted by a modulated carrier wave at the alternating current frequency.

Eddy current testing is based on an analysis of the phase displacement between the applied alternating current and the unbalance bridge voltage. This can be achieved by obtaining representations of the unbalance voltage components which are in phase with and in quadrature, or 90° out of phase, with the alternating current applied to the bridge.

It is known to display eddy current data on a display monitor in the form of monochrome strip chart waveforms of the two unbalanced voltage components. Such a display may be scrolled until an area of the display containing information of interest is lined up with a selected window. The stored information associated with that display area can be processed to produce a corresponding Lissajous figure representing the relationship between the quadrature and in-phase components associated with the display portion associated with the area of interest.

SUMMARY OF THE INVENTION

It is an object of the present invention to facilitate the study of eddy current test data.

Another object of the invention is to effect parallel display of time-coincident test data waveforms associated with different detector excitation frequencies.

Another object of the invention is to permit rapid switching from displays in strip chart form to displays in the form of Lissajous figures.

A further object of the invention is to permit rapid determination of Lissajous figure phase angles and peak amplitudes.

The above and other objects are achieved, according to the invention, by a method and apparatus for producing a display of eddy current test data from signals produced by an eddy current detector which is supplied with an alternating current signal composed of alternating currents at several different frequencies, the detector signals including a respective signal associated with each current frequency and varying in amplitude and in phase relative to its associated alternating current as the detector is displaced relative to a test body, the invention being implemented by: generating, from each detector signal, a data signal representing the detector signal component in phase with the associated alternating current and a data signal representing the detector signal component in quadrature with the associated alternating current; storing a representation of each data signal; and supplying the representation of each data signal to a display device for producing a first display composed of visible representations of all data signals along parallel axes, with each axis being associated with a respective data signal and being representative of the movement of the detector relative to the test body.

The alternating current applied to the detector contains several frequencies. By way of example, the alternating current may be composed of sinusoidal waves having frequencies, f, of 400 kHz, 100 kHz and 10 kHz so that the bridge unbalance voltage will be composed of three signals each a modulated version of the carrier wave at a respective one of these frequencies. Each frequency is useful for examining flaws at a different depth in the body being tested.

For each carrier frequency, f, the corresponding unbalance voltage signal will be divided into a component $Ex_f$ which is in phase with the associated carrier frequency, f, and a component $Ey_f$ which is in quadrature with the associated carrier frequency, f.

In addition, to eliminate unwanted signals, it can be useful to derive inphase and quadrature components based on a mixture of the components associated with several carrier frequencies. For example, the following component signals have been found to be useful for observing certain types of flaws:

$$Ex_{mix} = a \cdot Ex_{400} + b \cdot Ex_{100} + c \cdot Ey_{400} + d \cdot Ey_{100};$$

$$Ey_{mix} = e \cdot Ey_{400} + f \cdot Ey_{100} + g \cdot Ex_{400} + h \cdot Ex_{100};$$

where $Ex_{400}$ and $Ex_{100}$ are the in-phase components of the 400 kHz and 100 kHz unbalance voltage signals, $Ey_{400}$ and $Ey_{100}$ are the quadrature components of the 400 kHz and 100 kHz unbalance voltage signals, etc. The coefficients a-h are derived statistically, according to principles known in the art, under consideration of the particular body, the types of flaws to be observed, and the signals to be eliminated.

A display according to the invention can be in the form of a set of waveforms constituting strip charts constituting, respectively, the components associated with each alternating current frequency applied to the detector and the components derived from a mixture of the components associated with several carrier frequencies. The strip charts are preferably disposed side-by-side on the display with points associated with the same detector position being aligned perpendicular to the reference axes of the strip charts.

As desired, these strip charts can be replaced by a set of Lissajous figures each associated with a selected strip chart region, as will be described in greater detail below.

Each strip chart, or each Lissajous figure, can easily be adjusted with respect to its reference axis, or axes, and scaled as desired to permit evaluation of selected information.

The strip chart representations can be stepped forward and backward to permit examination of any desired area of the stored data.

With regard to the Lissajous figures, any range of an associated strip chart can be specified for derivation of the corresponding Lissajous figure, and the resulting figure can be positioned with respect to the selected set of coordinate axes and scaled as desired. Any angle on a Lissajous figure can be measured in a rapid and simple manner and the component values used to generate such a figure can be stepped forward and backward to illustrate the manner in which that particular figure was created.

DESCRIPTION OF THE PREFERRED EMBODIMENTS

The present invention utilizes an interactive color graphics display system to review eddy current test data in the form of strip charts or Lissajous figures. Each strip chart is based on a component of an unbalanced voltage signal associated with a particular detector excitation current frequency or a component of a mixture signal derived from the signals associated with several excitation current frequencies. Each excitation current frequency, or the mixture signal, is associated with two adjacent strip charts which represent, respectively, the in-phase component and the quadrature component of the associated signal.

Figure 1:
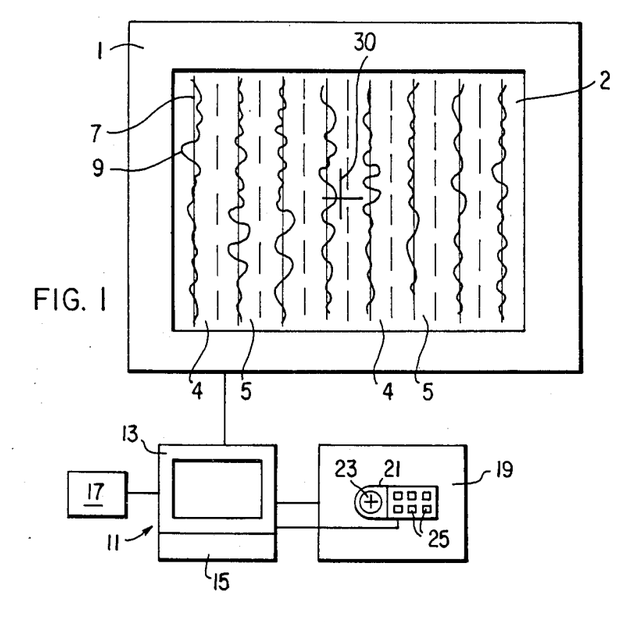
FIG. 1 is partly a block diagram and partly a pictorial view of a system for implementing the invention.

A strip chart display according to the invention is shown in FIG. 1, which illustrates a color graphics display device 1 having a display screen 2. The screen is divided into eight regions 4, 5, with each region displaying a vertical reference axis 7 and a waveform 9 constituting the associated strip chart.

A region 4 and the region 5 to the right thereof contain waveforms associated with corresponding in-phase and quadrature components derived from a respective unbalanced voltage signal from the eddy current detector or from the mixture of the components associated with several carrier frequencies. The region 4 displays the associated in-phase component, while the region 5 displays the associated quadrature component. Each vertical reference axis 7 corresponds to the path of displacement of the eddy current detector over the body being tested.

Screen 2 additionally displays a cursor representation 30 which can be displaced across the screen, in a manner to be described below, to identify a selected point in any screen region.

Display device 1 is associated with, and connected to, a control unit 11 composed of a monochrome monitor 13 for displaying text material and a keyboard 15 for controlling the input of information to display device 1. Control unit 11 is connected to a computer 17 in which the information for producing displays on screen 1 and the program for controlling the display are stored.

Also connected to unit 13 is an input device 19 for the input of information and directions by the user, primarily for the purpose of controlling the display on screen 2. The input device here represented is a graphics tablet which cooperates with a cursor 21 that is moveable over the surface of the graphics tablet to bring a cursor control element 23 to any selected point on the surface of the tablet.

Tablet 19 is linked to control unit 11 to cause movement of cursor 21 over the tablet surface to produce a corresponding displacement of cursor representation 30 on screen 2.

Cursor 21 is linked to control unit 11 and is provided with a plurality of function keys 25 which can be individually actuated to alter the display on screen 2 according to various functions.

All of the illustrated units can be constituted by known, commercially available devices. For example, an operative system according to the invention has been constructed utilizing, as computer 17, a Data General MV series computer, for control unit 11, a Data General Dasher D200 terminal, for display device 1, a Raster Technologies Model 120 color graphics display system, and for input device 19 and cursor 21, a GTCO Digi-Pad 5 graphics tablet with cursor.

In order to produce the desired displays, test data is derived in the usual manner and successive samples of each component signal are stored in digital form in computer 17. The data remains permanently stored during analysis.

Programming of the above-described system to perform all of the functions described herein can be easily developed and an exemplary program appears at the end of this specification. It is written in Fortran 77.

When cursor representation 30 is placed at a desired point on any one of waveforms 9, selected ones of function keys 25 can be actuated to selectively vary the zero position of that waveform, or its scale, or to select the start and end points for the information contained in an associated pair of waveforms which is to be used to produce a corresponding Lissajous figure.

Cursor representation 30 can also be placed on a selected axis 7 and a selected key 25 can be actuated to vary the scale of the display in the direction of waveform 9. Alternatively, keys 25 on keyboard 15 can be actuated to simultaneously vary the scales of all displays in the direction of their waveforms 9.

In addition, under control of keyboard 15, the vertical scale of all the data can be varied to permit a complete data set, i.e. data for an entire tube, or a limited amount of the data to be displayed. Furthermore, all of the waveforms can be stepped vertically in either direction. It is additionally possible to eliminate one or more waveform pairs, which will permit the speed with which the remaining strip charts are traced on screen 2 to be increased.

Preferably, all of the base information for the display on screen 2, that is, the reference axis markers and any other display elements which are independent of the data values themselves, is written on a single bit plane of the computer memory so that as the other information displayed on screen 2 is varied, the base information can remain constant.

In addition, it is preferable that the data corresponding to each waveform, or associated pair of waveforms, be stored in one image memory bank so that one such display on screen 2 does not have to be rewritten thereon when another display is altered.

Furthermore, it is preferable that each waveform have a respectively different color for ease of identification. This feature does not require any significant portion of the computer memory.

Figure 2:
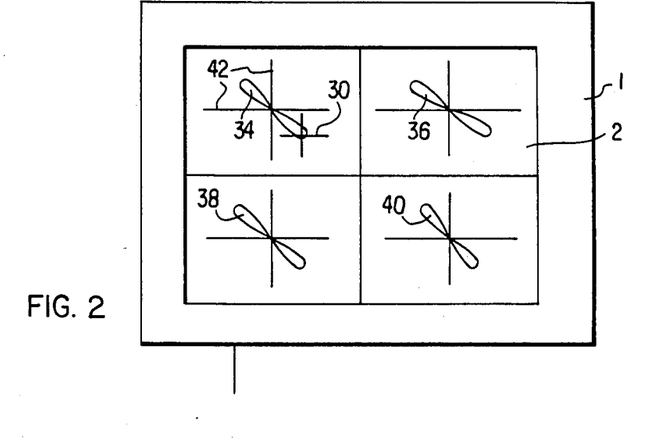
FIG. 2 is a pictorial view of part of the system of FIG. 1 producing a display different from that of FIG. 1.

After two end points along a selected reference axis 7 have been selected and indicated to the computer, by movement of cursor 21 and operation of appropriate function keys 25, the display on screen 2 can be changed from that shown in FIG. 1 to that shown in FIG. 2, where corresponding Lissajous figures are displayed for each associated pair of component signals. Thus, by way of example, Lissajous figure 34 represents the data associated with a selected portion of each of the first two strip charts 9, starting from the left, shown in FIG. 1 and derived, for example, from the bridge unbalance voltage signal associated with the alternating current frequency of 400 kHz. The other Lissajous figures 36, 38 and 40 are similarly associated with respective pairs of waveforms 9 and with the bridge unbalance voltage signals relating to the alternating current frequencies 100 kHz and 10 kHz, and with the component signals $Ex_{mix}$ and $Ey_{mix}$.

Cursor representation 30 continues to be displayed on screen 2 and is utilized to perform various operations on the Lissajous figure displays. For example, representation 30 can be utilized to center each Lissajous figure with respect to its associated reference axes 42 and/or to alter the scale of each figure. Representation 30 can additionally be utilized to provide a measurement of any angle of an associated Lissajous figure. All of these operations are performed under control of cursor 21 and function keys 25 (FIG. 1).

For example, in order to measure an angle, representation 30 is brought to the origin of the reference axes 42 and a first function key 25 is actuated. Representation 30 can then be moved to any position on the associated display and a line will appear on the display between the origin of the coordinate axes and the intersection of the lines of representation 30. By displacing representation 30, this line can be superimposed on any part of the Lissajous figure. When the line is properly superimposed, a second function key 25 is actuated and the inclination of the measuring line is indicated in numerical form on monitor 13.

Similarly, the vector amplitude of any point of a Lissajous figure can be measured by placing the intersection of the lines of representation 30 at the desired point on the figure and depressing another selected one of function keys 25. Then an indication of the vector amplitude value, in the form of a numerical value, is displayed on monitor 13.

Each Lissajous figure display 34, 36, 38 and 40 can be further controlled, by means of cursor 21 to permit the development of the Lissajous figure to be observed, i.e. successive segments of such a figure can be written onto screen 2.

As in the case of the waveforms 9 of FIG. 1, each of the Lissajous figures 34, 36, 38 and 40 of FIG. 2 can be displayed in a different color and the base information, i.e. the information for producing the vertical and horizontal lines dividing screen 2 into four quadrants and the reference axes for each figure can be stored in a single bit plane of the computer memory so that the associated information will remain constant.

In place of cursor 19, use could be made of a commercially available trackball or mouse. In this case, the function instructions could be provided by actuating selected keys of keyboard 15.

It will be understood that the above description of the present invention is susceptible to various modifications, changes and adaptations, and the same are intended to be comprehended within the meaning and range of equivalents of the appended claims.

```
           PROGRAM TEST
           CHARACTER*10 TITLE(8)
           DATA TITLE/
    &      '400 DIF   ',
    &      '400 DIF   ',
    &      '100 DIF   ',
    &      '100 DIF   ',
    &      ' 10 DIF   ',
    &      ' 10 DIF   ',
    &      '400 MIX   ',
    &      '400 MIX   '/
           CALL OPEN_DATA_FILE
           CALL SET_RANGE
           CALL SET_STRIP(TITLE,8)
           CALL RUN_STRIP_CHART
           END
           SUBROUTINE RUN_STRIP_CHART
           COMMON/DATA_POS/NSTEP,NP,NST(5),IST,NMAX,IDIR
           COMMON/RANGES/XMN(10),XMX(10)
           COMMON/STD_DEV_INFO/ XZERO(10),XSTDDEV(10)
           COMMON/DATA/ IDATA,ICL
           DIMENSION XLO(8),XHI(8)
           INTEGER*2 IDATA(3,51200)
           INTEGER*2 N1,N2
           DIMENSION ICL(3)
           DIMENSION CC(4),DD(4)
           DATA ICL/ 1, 2, 3, 4, 5, 6, 7, 8/
           DATA XZERO,XSTDDEV/20*0.0/
           NP=0
           open(205,
    &           file='STD.MIX',
    &           form="unformatted",
    &           iointent="input",
    &           iostat=ier,
    &           mode="binary",
    &           position="start",
    &           recfm="dynamic",
    &           status="old")
           if(ier.ne.0)STOP 'ERROR ON OPEN'
           READ(205)N1,N2,CC,DD
           CLOSE(205)
           DO 11 I=1,8
           IDATA(I,1)=IDATA(I,2)
           IDATA(I,NMAX+1)=IDATA(I,NMAX)
           DO 12 J=1,NMAX
           IDATA(7,J)=    CC(1)*IDATA(2*N1-1,J)+
    &                    CC(2)*IDATA(2*N1  ,J)+
    &                    CC(3)*IDATA(2*N2-1,J)+
    &                    CC(4)*IDATA(2*N2  ,J)
           IDATA(8,J)=    DD(1)*IDATA(2*N1-1,J)+
```

```
                   DD(2)*IDATA(2*N1  ,J)+
                   DD(3)*IDATA(2*N2-1,J)+
                   DD(4)*IDATA(2*N2  ,J)
 CONTINUE
 CALL STD_DEV(IDATA,8,NMAX)
 CALL ENTGRA
 CALL MENU_STRIP
 CALL TABLET_READ_STILL
 CONTINUE
 IF(IDIR*NSTEP+NP.LE.0.OR.IDIR*NSTEP+NP.GE.NMAX)THEN
         CALL TABLET_READ(1)
 ELSE
         IF(MOD(NP+100,100).EQ.0)CALL TABLET_READ(0)
         DO 3 I=1,8
         X1=(REAL(IDATA(I,NP+1))+REAL(IDATA(I,NP+2)))/2.-XZERO(I)
         X2=IDATA(I,NP+2)-XZERO(I)
         X3=(REAL(IDATA(I,NP+1+NSTEP))+REAL(IDATA(I,NP+2+NSTEP)))
          /2.-XZERO(I)
         XLO(I)=AMIN1(X1,X2,X3)
         XHI(I)=AMAX1(X1,X2,X3)
         DO 5 J=2,NSTEP
         DO 5 I=1,8
         X1=IDATA(I,NP+1+J)-XZERO(I)
         XLO(I)=AMIN1(XLO(I),X1)
         XHI(I)=AMAX1(XHI(I),X1)
         CALL STRIP_SUB(XLO,XHI,ICL,8)
         NP=NP+NSTEP*IDIR
 ENDIF
 GO TO 2
 END
 SUBROUTINE SET_RANGE
 COMMON/RANGES/XMN(10),XMX(10)
 XMAX=3.
 DO 1 I=1,10
 XMN(I)=-XMAX*1638.3
 XMX(I)=XMAX*1638.3
 RETURN
 END
 SUBROUTINE OPEN_DATA_FILE
 COMMON/DATA_POS/NSTEP,NP,NST(5),IST,NMAX,IDIR
 COMMON/DATA/IDATA,ICL
 INTEGER*2 IDATA(8,51200)
 DIMENSION ICL(8)
 CHARACTER*130 IFILE
 PRINT*,'ENTER DATA FILE NAME : '
 READ(5,'(A)')IFILE
 IF(IFILE.EQ.' ')STOP
 CALL GET_DATA(IFILE,IDATA(1,2),8*51199,NVALS)
 NMAX=NVALS/8
 RETURN
 END
 SUBROUTINE GET_DATA(FILE,IDATA,N,NV)
 THIS ROUTINE READS THE PLOT DATA FROM FILE INTO IDATA
 INTEGER*2 IDATA(N)
 CHARACTER*(*) FILE
 NB=16
 LL=LSTRING(FILE)
 CALL BOPEN(FILE(:LL)//'<0>',NB,IER)
 IF(IER.NE.0)THEN
         PRINT*,'ERROR ON OPEN ',IER
         STOP
 ENDIF
 IP=1
 IB=0
 NCS=NB*512
 CALL BREAD(IDATA(IP),NCS,IB,IER)
 IF(NCS.NE.NB*512)GO TO 2
 IB=IB+NB
 IP=IP+NB*256
 GO TO 1
 NCT=NCS+IB*512
 NV=NCT/2
 RETURN
 END
 SUBROUTINE TABLET_READ(ISTAT)
 COMMON/SCREEN_POS/IC,NCOLPS,NCOLPS2,NCOLPS3,NCOLPS1
 COMMON/DATA_POS/NSTEP,NP,NST(5),IST,NMAX,IDIR
 COMMON/RANGES/XMN(10),XMX(10)
 CHARACTER*1 ANS
 DATA NSTEP/10/
 DATA NST/1,2,5,10,20/
 DATA IST/4/
 DATA IDIR/1/
 ISTOP=ISTAT
 LX1=0
```

```
      CALL READBUT(ISTOP,1,IBUT,IX,IY)
      ISTOP=0
      GO TO(1,2,3,4,5,6,7,8,9,10,11,12,13)IBUT
      RETURN
1     CALL CHANGE_DIR
      GO TO 99
2     GO TO 99
3     GO TO 99
4     GO TO 99
5     GO TO 99
6     GO TO 99
7     GO TO 99
8     GO TO 99
9     GO TO 99
10    GO TO 99
11    CALL QUIT
      PRINT*,'ENTER LOCATION (0 TO QUIT) [0] '
      READ(5,'(I20)')ILOC
      IF(ILOC.EQ.0)STOP
      IF(ILOC.LT.0)ILOC=1
      IF(ILOC.GT.NMAX)ILOC=NMAX
      NP=ILOC+IDIR*NSTEP*232
      CALL ENTGRA
      CALL STILL_STRIP_CHART(0)
      GO TO 99
12    CALL TABLET_READ_STILL
      GO TO 99
99    END
      SUBROUTINE CHANGE_DIR
      COMMON/DATA_POS/NSTEP,NP,NST(5),IST,NMAX,IDIR
      COMMON/SCREEN_POS/IC,NCOLPS,NCOLPS2,NCOLPS3,NCOLPS1
      IF(NP-464*NSTEP*IDIR.LT.1)RETURN
      CALL MOVREL(0,-464*IDIR)
      NP=NP-464*NSTEP*IDIR
      IC=IC-464*IDIR
      IDIR=-IDIR
      CALL CLOAD(21,0,IDIR)
      RETURN
      END
      SUBROUTINE SET_STRIP(TITLE,N)
      COMMON/SCREEN_POS/IC,NCOLPS,NCOLPS2,NCOLPS3,NCOLPS1
      CHARACTER*(*) TITLE(N)
      NCOLPS=512/N
      NCOLPS1=NCOLPS-1
      NCOLPS2=NCOLPS/2
      NCOLPS3=NCOLPS-3
      IC=51200
      CALL INITOU(200,'BOUTPUT',7)
      CALL ENTGRA
      CALL BUTTBL(0,0)
      CALL WRMASK(255,7)
      CALL VAL3(0)
      CALL FLOOD
      CALL VAL3(255)
      CALL LISS_SET
      CALL VAL3(255)
      CALL WRMASK(128,1)
C          DRAW CENTER LINES
      DO 4 I=1,N
      III=I*NCOLPS-256-NCOLPS2
      CALL MOVABS(III,255)
4     CALL DRWREL(0,-512)
C          END CENTER LINES
C          OUTLINE EACH CHART
      CALL MOVABS(-255,-256)
      DO 7 I=1,N
      CALL DRWREL(0,512)
      CALL MOVREL(NCOLPS3,0)
      CALL DRWREL(0,-512)
7     CALL MOVREL(3,0)
C          END OF OUTLINE
      CALL OVRVAL(0,1)
      CALL OVRVAL(1,1)
      CALL WRMASK(255,3)
      CALL VLOAD(5,0,0,0)
      CALL VLOAD(4,0,255,255)
C          OUTLINE EACH CHART
      CALL MOVABS(-256,-240)
      DO 8 I=1,N
      CALL DRWREL(0,512)
      CALL MOVREL(NCOLPS1,0)
      CALL DRWREL(0,-512)
8     CALL MOVREL(1,0)
C          END OF OUTLINE
      CALL PRMFIL(1)
```

```
      CALL MOVABS(-256,-256)
      CALL RECTAN(255,-240)
      CALL WRMASK(255,16)
      CALL PRMFIL(0)
      CALL RECTAN(255,-240)
      CALL MOVREL(42,5)
      CALL TEXT1(10,TITLE(1))
      DO 2 I=3,N-1,2
      CALL MOVREL(NCOLPS*2,0)
    2 CALL TEXT1(10,TITLE(I))
      CALL WRMASK(255,3)
      CALL PRMFIL(1)
      CALL MOVABS(-256,220)
      CALL RECTAN(255,255)
      CALL WRMASK(255,16)
      CALL PRMFIL(0)
      CALL RECTAN(255,255)
      CALL MOVREL(42,14)
      CALL TEXT1(10,TITLE(1))
      DO 3 I=3,N-1,2
      CALL MOVREL(NCOLPS*2,0)
    3 CALL TEXT1(10,TITLE(I))
      CALL MOVABS(-156,246)
      CALL CRIGHT
      CALL MOVABS(-253,231)
      CALL AILOGO
      CALL MACRO_DEFINITION_1
      CALL MACRO_DEFINITION_2
      CALL MACRO_DEFINITION_3
      CALL MACRO_DEFINITION_4
      CALL MACRO_DEFINITION_5
      CALL MACRO_DEFINITION_6
      CALL MACRO_DEFINITION_7
      CALL MACRO_DEFINITION_8
      CALL CLOAD(21,0,1)
      CALL CLOAD(23,-256,225)
      CALL CLOAD(24,0,0)
      CALL MACRO(2)
      CALL MACRO(5)
      DO 33 I=1,N
      III=I
   33 CALL WRITE_RANGE(III)
      CALL QUIT
      RETURN
      END
      SUBROUTINE MACRO_DEFINITION_1
      CALL MACDEF(1)                  !MOVE SCREEN AND CURSOR
      CALL CADD(0,21)
      CALL CADD(4,21)
      CALL CMOVE(23,0)
      CALL CMOVE(24,4)
      CALL MACEND
      RETURN
      END
      SUBROUTINE MACRO_DEFINITION_2
      CALL MACDEF(2)                  !DEFINE COLORS
      CALL LUTRTE(83)
      CALL WRMASK(127,1)
      CALL OVRRD(0,1)
      CALL OVRRD(1,1)
      CALL VAL8(12)
      CALL CMOVE(0,23)
      CALL CMOVE(4,24)
      CALL MACEND
      RETURN
      END
      SUBROUTINE MACRO_DEFINITION_3
      CALL MACDEF(3)
      CALL CMOVE(5,2)
      CALL MACEND
      RETURN
      END
      SUBROUTINE MACRO_DEFINITION_4
      CALL MACDEF(4)           !LISSAJOUS MACRO
      CALL WRMASK(63,2)
      CALL LUTRTE(117)
      CALL OVRRD(0,0)
      CALL OVRRD(1,0)
      CALL MACEND
      RETURN
      END
      SUBROUTINE MACRO_DEFINITION_5
      CALL MACDEF(5)
      CALL LUTRMP(1,64,127,62,62)
      CALL LUTRMP(1,192,255,62,62)
      CALL LUTRMP(2,64,127,200,200)
```

```
      CALL LUTRMP(2,192,255,200,200)
      CALL LUTRMP(4,64,127,255,255)
      CALL LUTRMP(4,192,255,255,255)
      CALL LUT8(1,255,0,0)
      CALL LUT8(2,255,0,0)
      CALL LUT8(3,50,5,155)
      CALL LUT8(4,50,50,255)
      CALL LUT8(5,220,220,0)
      CALL LUT8(6,220,220,0)
      CALL LUT8(7,255,0,150)
      CALL LUT8(8,255,0,150)
      CALL LUT8(9,50,40,12)
      CALL LUT8(10,75,60,19)
      CALL LUT8(11,100,80,25)
      CALL LUT8(12,250,200,62)
      DO 1 I=1,51
      P=MOD((I+33),50)*.02
      P=1.-P
      CALL SPECT(P,IR,IG,IB)
      CALL LUT8(12+I,IR,IG,IB)
   1  CALL LUT8(12+I,IR,IG,IB)
      CALL LUT8(128,200,160,50)
      CALL LUT8(128+1,255,0,0)
      CALL LUT8(128+2,255,0,0)
      CALL LUT8(128+3,50,50,255)
      CALL LUT8(128+4,50,50,255)
      CALL LUT8(128+5,220,220,0)
      CALL LUT8(128+6,220,220,0)
      CALL LUT8(128+7,255,0,150)
      CALL LUT8(128+8,255,0,150)
      CALL LUT8(128+9,150,120,37)
      CALL LUT8(128+10,150,120,37)
      CALL LUT8(128+11,150,120,37)
      CALL LUT8(128+12,250,200,62)
      CALL MACEND
      RETURN
      END
      SUBROUTINE MACRO_DEFINITION_6
      CALL MACDEF(6)
      CALL WRMASK(64,2)
      CALL VAL8(0)
      CALL CLEAR
      CALL BUTTBL(0,7)
      CALL XHAIR(0,0)
      CALL MACEND
      RETURN
      END
      SUBROUTINE MACRO_DEFINITION_7
      CALL MACDEF(7)
      CALL VAL8(0)
      CALL CMOVE(0,30)
      CALL DRWI(31)
      CALL CMOVE(0,30)
      CALL VAL8(64)
      CALL CMOVE(31,2)
      CALL DRWI(31)
      CALL MACEND
      RETURN
      END
      SUBROUTINE MACRO_DEFINITION_8
      CALL MACDEF(8)
      CALL WRMASK(63,2)
      CALL BUTTBL(0,3)
      CALL XHAIR(0,1)
      CALL MACEND
      RETURN
      END
      SUBROUTINE WRITE_RANGE(ISTRIP)
      SAVE CAX
      COMMON/RANGES/XMN(10),XMX(10)
      CHARACTER*10 CPOS
      CHARACTER*2 CAX(2)
      COMMON/SCREEN_POS/IC,NCOLPS,NCOLPS2,NCOLPS3,NCOLPS1
      DATA CAX/"Y ","X "/
      CALL WRMASK(255,16)
      CALL OVRVAL(0,0)
      CALL CMOVE(22,0)
      CALL MOVABS(-240+(ISTRIP-1)*NCOLPS,222)
      CALL PRMFIL(1)
      CALL RECREL(NCOLPS-20,6)
      CALL OVRVAL(0,1)
      WRITE(CPOS,'(F5.2)')XMX(ISTRIP)/1638.3
      CALL TEXT1(8,CAX(1+MOD(ISTRIP,2))//CPOS)
      CALL WRMASK(127,1)
      CALL CMOVE(0,22)
      RETURN
      END
```

```
      SUBROUTINE STRIP_SUB(XLO,XHI,ICL,N)
      COMMON/RANGES/XMN(10),XMX(10)
      COMMON/DATA_POS/NSTEP,NP,NST(5),IST,NMAX,IDIR
      CHARACTER*5 CPOS
      COMMON/SCREEN_POS/IC,NCOLPS,NCOLPS2,NCOLPS3,NCOLPS1
      DIMENSION XLO(N),XHI(N),ICL(N)
      NWIDTH=NCOLPS*N
      IOFFL=0
      IC3=0
      INUM=NP-IDIR*4*NSTEP
      IF(MOD(INUM+200,200).EQ.0)THEN
             IF(MOD(INUM+1000,1000).EQ.0.OR.NSTEP.LT.20)THEN
                   CALL CMOVE(22,0)
                   IY=MOD(990+IC-4*IDIR,512)-256
                   WRITE(CPOS,"(I5.5)")INUM
                   CALL MOVABS(-253,IY)
                   CALL TEXT1(5,CPOS)
                   IF(IY.GT.240)THEN
                         CALL MOVREL(0,-512)
                         CALL TEXT1(5,CPOS)
                   ENDIF
                   CALL CMOVE(0,22)
             ENDIF
      ENDIF
      IF(MOD(NP+10,10).EQ.0)THEN
             IF(MOD(NP+50,50).EQ.0)THEN
                   IF(MOD(NP+100,100).EQ.0)THEN
                         IC3=11
                   ELSE
                         IF(NSTEP.LT.10)IC8=10
                   ENDIF
             ELSE
                   IF(NSTEP.LT.2)IC3=9
             ENDIF
      ENDIF
      IC=IC+IDIR
      CALL RN8HDR(1,NWIDTH)
      DO 1 I=1,N
      IXLO=MAX(0,MIN(NCOLPS1,1+INT(NCOLPS3*(XLO(I)-XMN(I))/(XMX(I)
     &                                                  -XMN(I)))))
      IXHI=MAX(0,MIN(NCOLPS1,1+INT(NCOLPS3*(XHI(I)-XMN(I))/(XMX(I)
     &                                                  -XMN(I)))))
      IOFF=IOFFL+IXLO
      IOFFL=NCOLPS1-IXHI
      ION=IXHI-IXLO+1
      IF(IOFF.GT.0)CALL RN8STR(IC8,IOFF)
      CALL RN8STR(ICL(I),ION)
      IF(IOFFL.GT.0)CALL RN8STR(IC3,IOFFL)
      CALL MACRO(1)
      RETURN
      END
      SUBROUTINE TABLET_READ_STILL
      COMMON/STD_DEV_INFO/ XZERO(10),XSTODEV(10)
      COMMON/SCREEN_POS/IC,NCOLPS,NCOLPS2,NCOLPS3,NCOLPS1
      COMMON/DATA_POS/NSTEP,NP,NST(5),IST,NMAX,IDIR
      COMMON/RANGES/XMN(10),XMX(10)
      COMMON/CHANGES/ICHANGE(8)
      CHARACTER*1 ANS
      DATA ICHANGE/8*0/
      IPAUSE=0
      IDIRS=IDIR
      IF(IDIR.EQ.-1)CALL CHANGE_DIR
      IDIR=1
      CALL BUTTBL(0,3)
      CALL XHAIR(0,1)
      IF(NP.EQ.0.AND.IDIR.EQ.1)GO TO 97
      CALL READBUT(1,1,IBUT,IX,IYY)
      ISTRIP=0
      IY=MOD(IC+225-IYY,512)
      CALL CLOAD(5,512,0)
      GO TO(1,2,3,4,5,6,7,8,9,10,11,12,13)IBUT
      RETURN
      IDIRS=-IDIRS
      GO TO 98
      IST=MAX(1,IST-1)
      NPC=NP-232*NSTEP
      NSTEP=NST(IST)
      NP=NPC+232*NSTEP
      GO TO 97
      IST=MIN(5,IST+1)
      NPC=NP-IY*NSTEP
      NSTEP=NST(IST)
      NP=NPC+NSTEP*232
      GO TO 97
      IST=1
      NPC=NP-IY*NSTEP
      NSTEP=NST(IST)
```

```
      NP=NPC+NSTEP*232
      GO TO 97
      ISTRIP=MAX(1,MIN(8,(IX+255+NCOLPS)/NCOLPS))
      XMX(ISTRIP)=XMX(ISTRIP)/2.
      XMN(ISTRIP)=XMN(ISTRIP)/2.
      CALL WRITE_RANGE(ISTRIP)
      ICHANGE(ISTRIP)=ICHANGE(ISTRIP)+1
      GO TO 99
      ISTRIP=MAX(1,MIN(8,(IX+255+NCOLPS)/NCOLPS))
      XMX(ISTRIP)=XMX(ISTRIP)*2.
      XMN(ISTRIP)=XMN(ISTRIP)*2.
      CALL WRITE_RANGE(ISTRIP)
      ICHANGE(ISTRIP)=ICHANGE(ISTRIP)-1
      GO TO 99
      CALL CMOVE(30,0)
      CALL MOVABS(-256,IYY)
      CALL WRMASK(64,1)
      CALL VAL8(64)
      CALL DRWREL(512,0)
      CALL READBUT(1,1,IBUT,IXX,IYY2)
      CALL MOVABS(-256,IYY2)
      CALL DRWREL(512,0)
      IY2=MOD(IC+225-IYY2,512)
      NP1=NP-IY*NSTEP
      NP2=NP-IY2*NSTEP
      CALL TABLET_READ_LISSAJOUS(NP1,NP2)
      CALL WRMASK(64,1)
      CALL VAL8(0)
      CALL CMOVE(0,30)
      CALL CLEAR
      CALL VAL8(12)
      CALL WRMASK(127,1)
      CALL MENU_STRIP
      DO 70 I=1,8
      III=I
      IF(ICHANGE(I).NE.0)CALL WRITE_RANGE(III)
      GO TO 99
      NP=NP-NSTEP*400
      GO TO 97
      NP=NP+NSTEP*400
      GO TO 97
      ISTRIP=MAX(1,MIN(8,(IX+255+NCOLPS)/NCOLPS))
      XOFF=XMN(ISTRIP)+(256+IX-(ISTRIP-1)*NCOLPS-1)*
     (XMX(ISTRIP)-XMN(ISTRIP))/(NCOLPS3)
      XZERO(ISTRIP)=XZERO(ISTRIP)+XOFF
      ICHANGE(ISTRIP)=100
      GO TO 99
      IPAUSE=1-IPAUSE
      GO TO 99
      CALL QUIT
      PRINT*,'ENTER LOCATION (0 TO QUIT) [0] '
      READ(5,'(I20)')ILOC
      IF(ILOC.EQ.0)STOP
      IF(ILOC.LT.0)ILOC=1
      IF(ILOC.GT.NMAX)ILOC=NMAX
      NP=ILOC+IDIR*NSTEP*232
      CALL ENTGRA
      GO TO 97
      DO 94 I=1,8
      IF(ICHANGE(I).NE.0)THEN
           III=I
           CALL STILL_STRIP_CHART(III)
           ICHANGE(I)=0
      ENDIF
      CONTINUE
      IF(IDIRS.EQ.-1)CALL CHANGE_DIR
      CALL QUIT
      CALL ENTGRA
      CALL BUTT8L(0,0)
      CALL XHAIR(0,0)
      CALL CLOAD(5,512,0)
      RETURN
      DO 96 I=1,8
      ICHANGE(I)=1000
      NP=MIN(NMAX,MAX(NP,464*NSTEP))
      NP=(NP/NSTEP)*NSTEP
      CALL VAL8(0)
      CALL CLEAR
      IC=51200
      IF(IC.NE.51200)GO TO 97
      IF(NP.NE.(NP/NSTEP)*NSTEP)GO TO 97
      DO 95 I=1,8
      CALL READBUT(IPAUSE,1,IBUT,IX,IYY)
      IY=MOD(IC+225-IYY,512)
      GO TO(1,2,3,4,5,6,7,8,9,10,11,12,13)IBUT
      IF(ICHANGE(I).NE.0)THEN
           III=I
```

```
              CALL STILL_STRIP_CHART(III)
              ICHANGE(I)=0
      ENDIF
      CONTINUE
      GO TO 98
      END
      SUBROUTINE STILL_STRIP_CHART(ISTRIP)
      COMMON/SCREEN_POS/IC,NCOLPS,NCOLPS2,NCOLPS3,NCOLPS1
      COMMON/DATA_POS/NSTEP,NP,NST(5),IST,NMAX,IDIR
      COMMON/RANGES/XMN(10),XMX(10)
      COMMON/STD_DEV_INFO/ XZERO(10),XSTDDEV(10)
      COMMON/DATA/IDATA,ICL
      COMMON/CHANGES/ICHANGE(8)
      INTEGER*2 IDATA(8,51200)
      DIMENSION XLO(8,512),XHI(8,512)
      DIMENSION ICL(8)
      IF(ISTRIP.EQ.0)THEN
              ISTART=1
              IEND=8
      ELSE
              ISTART=ISTRIP
              IEND=ISTRIP
      ENDIF
      NPS=NP
      N2=464
      NP=MIN(NMAX,MAX(NP,N2*NSTEP))
      NP=(NP/NSTEP)*NSTEP
      IF(NPS.NE.NP.OR.IC.NE.51200)THEN
              ISTART=1
              IEND=8
      ENDIF
      DO 1 I=ISTART,IEND
      ICHANGE(I)=0
      IF(NMAX/NSTEP.LT.N2)N2=NMAX/NSTEP
      NTOP=NP
      CALL VAL8(0)
      CALL WINDOW((ISTART-1)*NCOLPS-256,-256,IEND*NCOLPS-257,255)
      CALL CLEAR
      CALL WINDOW(-256,-256,255,255)
      CALL CLOAD(23,-256,225)
      CALL CLOAD(24,0,0)
      CALL CMOVE(0,23)
      CALL SCRORG(0,0)
      DO 2 IL=1,N2
      DO 3 I=ISTART,IEND
      X1=(REAL(IDATA(I,NP+1))+REAL(IDATA(I,NP+2)))/2.-XZERO(I)
      X2=IDATA(I,NP+2)-XZERO(I)
      X3=(REAL(IDATA(I,NP+1+NSTEP))+REAL(IDATA(I,NP+2+NSTEP)))/2.
     &                                                 -XZERO(I)
      XLO(I,IL)=AMIN1(X1,X2,X3)
      XHI(I,IL)=AMAX1(X1,X2,X3)
      DO 5 J=2,NSTEP
      DO 5 I=ISTART,IEND
      X1=IDATA(I,NP+1+J)-XZERO(I)
      XLO(I,IL)=AMIN1(XLO(I,IL),X1)
      XHI(I,IL)=AMAX1(XHI(I,IL),X1)
      NP=NP-NSTEP
      CONTINUE
      NP=NTOP
      CALL STRIP_SUB_STILL(XLO,XHI,ICL,8,N2,ISTART,IEND)
      RETURN
      END
      SUBROUTINE STRIP_SUB_STILL(XLO,XHI,ICL,N1,N2,ISTART,IEND)
      COMMON/RANGES/XMN(10),XMX(10)
      COMMON/DATA_POS/NSTEP,NP,NST(5),IST,NMAX,IDIR
      CHARACTER*5 CPOS
      COMMON/SCREEN_POS/IC,NCOLPS,NCOLPS2,NCOLPS3,NCOLPS1
      DIMENSION XLO(N1,N2),XHI(N1,N2),ICL(N1)
      NWIDTH=NCOLPS*(1+IEND-ISTART)
      CALL MOVREL((ISTART-1)*NCOLPS,0)
      CALL RN8HDR(N2,NWI,T-)
      IOFFL=0
      ICBL=0
      DO 2 JJ=1,N2
      NPP=NP-NSTEP*(JJ-1)
      IC8=0
      IF(MOD(NPP+10,10).EQ.0)THEN
              IF(MOD(NPP+50,50).EQ.0)THEN
                      IF(MOD(NPP+100,100).EQ.0)THEN
                              IC8=11
                      ELSE
                              IF(NSTEP.LT.10)IC8=10
                      ENDIF
              ELSE
                      IF(NSTEP.LT.2)IC8=9
              ENDIF
```

```
      ENDIF
      DO 1 I=ISTART,IEND
      IXLO=MAX(0,MIN(NCOLPS1,1+INT(NCOLPS3*(XLO(I,JJ)-XMN(I))/(XMX(I)
     &                -XMN(I)))))
      IXHI=MAX(0,MIN(NCOLPS1,1+INT(NCOLPS3*(XHI(I,JJ)-XMN(I))/(XMX(I)
     &                -XMN(I)))))
      IF(ICB.NE.ICBL)THEN
             IF(IOFFL.GT.0)CALL RN8STR(ICBL,IOFFL)
             IOFFL=0
             ICBL=ICB
      ENDIF
      IOFF=IOFFL+IXLO
      IOFFL=NCOLPS1-IXHI
      ION=IXHI-IXLO+1
      IF(IOFF.GT.0)CALL RN8STR(ICB,IOFF)
      CALL RN8STR(ICL(I),ION)
      CONTINUE
      IF(IOFFL.GT.0)CALL RN8STR(ICBL,IOFFL)
      IC=51200
      CALL VAL8(12)
      IF(ISTART.EQ.1)THEN
             DO 3 JJ=1,N2
             NPP=NP-NSTEP*(JJ-1)
             INUM=NPP-4*NSTEP
             IF(MOD(INUM+200,200).EQ.0)THEN
                    IF(MOD(INUM+1000,1000).EQ.0.OR.NSTEP.LT.20)THEN
                           CALL CMOVE(22,0)
                           IY=MOD(936+IC,512)-256
                           WRITE(CPOS,'(I5.5)')INUM
                           CALL MOVABS(-253,IY)
                           CALL TEXT1(5,CPOS)
                           IF(IY.GT.240)THEN
                                  CALL MOVREL(0,-512)
                                  CALL TEXT1(5,CPOS)
                           ENDIF
                           CALL CMOVE(0,22)
                    ENDIF
             ENDIF
             IC=IC-1
             CONTINUE
             IC=51200
      ENDIF
      CALL MOVREL((1-ISTART)*NCOLPS,0)
      RETURN
      END
      SUBROUTINE LISSAJOUS(ISTRIP,NP1,NP2)
      COMMON/LISSAJOUS_RANGES/ IXMIN(5),IYMIN(5)
      COMMON/STD_DEV_INFO/ XZERO(10),XSTDDEV(10)
      COMMON/DATA/IDATA,ICL
      COMMON/RANGES/XMN(10),XMX(10)
      INTEGER*2 IDATA(8,51200)
      DATA IXMIN,IYMIN/-243,8,8,-248,84,-16,-16,-256,-256,-171/
      CALL WRMASK(63,2)
      CALL VAL8(0)
      IF(ISTRIP.EQ.0)THEN
             IFIRST=1
             ILAST=4
      ELSE
             IFIRST=ISTRIP
             ILAST=ISTRIP
             CALL WINDOW(IXMIN(ISTRIP),IYMIN(ISTRIP),
     &             IXMIN(ISTRIP)+240,IYMIN(ISTRIP)+240)
      ENDIF
      CALL CLEAR
      CALL WINDOW(-256,-256,255,255)
      DO 1 I=IFIRST,ILAST
      III=I*2
      CALL VAL8(III)
      CALL MOVABS(120+IXMIN(I),120+IYMIN(I))
      CALL WINDOW(IXMIN(I)+1,IYMIN(I)+1,
     &    IXMIN(I)+239,IYMIN(I)+239)
      II=I*2-1
      I2=I*2
      X=IDATA(II,NP1)-XZERO(II)
      Y=IDATA(I2,NP1)-XZERO(I2)
      IXL=MAX(0,MIN(240,1+INT(238*(X-XMN(II))/(XMX(II)-XMN(II)))))-120
      IYL=MAX(0,MIN(240,1+INT(238*(Y-XMN(II))/(XMX(II)-XMN(II)))))-120
      CALL MOVREL(IXL,IYL)
      DO 2 J=NP1+1,NP2
      X=IDATA(II,J)-XZERO(II)
      Y=IDATA(I2,J)-XZERO(I2)
      IXC=MAX(0,MIN(240,1+INT(238*(X-XMN(II))/(XMX(II)-XMN(II)))))-120
      IYC=MAX(0,MIN(240,1+INT(238*(Y-XMN(II))/(XMX(II)-XMN(II)))))-120
      CALL DRWREL(IXC-IXL,IYC-IYL)
      IXL=IXC
      IYL=IYC
      CONTINUE
```

```
      CALL WINDOW(-256,-256,255,255)
      CONTINUE
      RETURN
      END
      SUBROUTINE TABLET_READ_LISSAJOUS(NP1,NP2)
      COMMON/STD_DEV_INFO/ XZERO(10),XSTDDEV(10)
      COMMON/SCREEN_POS/IC,NCOLPS,NCOLPS2,NCOLPS3,NCOLPS1
      COMMON/DATA_POS/NSTEP,NP,NST(5),IST,NMAX,IDIR
      COMMON/RANGES/XMN(10),XMX(10)
      COMMON/LISSAJOUS_RANGES/ IXMIN(5),IYMIN(5)
      COMMON/CHANGES/ICHANGE(8)
      CHARACTER*1 ANS
      CHARACTER*3 CDEG
      CALL MACRO(4)
      CALL PRMFIL(0)
      CALL SCRORG(0,0)
      CALL MENU_LISS
      IF(NP1.LT.NP2)THEN
              NPF=NP1
              NPL=NP2
      ELSE
              NPF=NP2
              NPL=NP1
      ENDIF
      NPFS=NPF
      NPLS=NPL
      CALL LISSAJOUS(0,NPF,NPL)
      CALL READBUT(1,1,IBUT,IX,IY)
      ISTRIP=0
      NPC=(NPF+NPL)/2
      NPD=NPL-NPF
      GO TO(1,2,3,4,5,6,7,8,9,10,11,12,13)IBUT
      RETURN
      DO 110 I=1,4
      IF(IX.LT.IXMIN(I).OR.IX.GT.IXMIN(I)+255)GO TO 110
      IF(IY.LT.IYMIN(I).OR.IY.GT.IYMIN(I)+255)GO TO 110
      ISTRIP=I
      GO TO 111
      CONTINUE
      GO TO 98
      CALL WINDOW(IXMIN(ISTRIP),IYMIN(ISTRIP),
     &            IXMIN(ISTRIP)+256,IYMIN(ISTRIP)+256)
      CALL CMOVE(32,0)
      CALL CLOAD(30,IX,IY)
      CALL CMOVE(31,30)
      CALL MACRO(6)
      CALL READBUT(1,1,IBUT,IX2,IY2)
      CALL MACRO(8)
      CALL CMOVE(0,32)
      CALL WINDOW(-256,-256,255,255)
      DX=IX2-IX
      DY=IY2-IY
      IF(DY.LT.0.)THEN
              DY=-DY
              DX=-DX
              IX2=IX1
              IY2=IY1
      ENDIF
      CALL GET_POLAR(DX,DY,DR,DTH)
      IDTH=DTH+.5
      IDTH=MOD(IDTH+360,360)
      CALL MOVABS(IX2-30,IY2+5)
      WRITE(CDEG,"(I3)")180-IDTH
      CALL WRMASK(64,2)
      CALL TEXT1(11,CDEG//" Degrees")
      CALL WRMASK(63,2)
      GO TO 98
      NPF=NPC-NPD/4
      NPL=NPC+NPD/4
      GO TO 99
      NPF=MAX(1,NPC-NPD)
      NPL=MIN(NMAX,NPC+NPD)
      GO TO 99
      NPF=NPFS
      NPL=NPLS
      GO TO 99
      DO 50 I=1,5
      IF(IX.LT.IXMIN(I).OR.IX.GT.IXMIN(I)+239)GO TO 50
      IF(IY.LT.IYMIN(I).OR.IY.GT.IYMIN(I)+239)GO TO 50
      ISTRIP=I
      ICHANGE(ISTRIP*2-1)=ICHANGE(ISTRIP*2-1)+1
      ICHANGE(ISTRIP*2)=ICHANGE(ISTRIP*2-1)
      GO TO 51
      CONTINUE
      GO TO 98
      XMX(ISTRIP*2-1)=XMX(ISTRIP*2-1)*2.
```

```
      XMN(ISTRIP*2-1)=XMN(ISTRIP*2-1)*2.
      XMX(ISTRIP*2)=XMX(ISTRIP*2-1)
      XMN(ISTRIP*2)=XMN(ISTRIP*2-1)
      GO TO 99
      DO 60 I=1,5
      IF(IX.LT.IXMIN(I).OR.IX.GT.IXMIN(I)+239)GO TO 60
      IF(IY.LT.IYMIN(I).OR.IY.GT.IYMIN(I)+239)GO TO 60
      ISTRIP=I
      GO TO 61
   60 CONTINUE
      GO TO 98
   61 XMX(ISTRIP*2-1)=XMX(ISTRIP*2-1)/2.
      XMN(ISTRIP*2-1)=XMN(ISTRIP*2-1)/2.
      XMX(ISTRIP*2)=XMX(ISTRIP*2-1)
      XMN(ISTRIP*2)=XMN(ISTRIP*2-1)
      ICHANGE(ISTRIP*2-1)=ICHANGE(ISTRIP*2-1)-1
      ICHANGE(ISTRIP*2)=ICHANGE(ISTRIP*2-1)
      GO TO 99
      CALL COLOR_STRIP_CHART(NPF,NPL)
      CALL LUTRTE(117)
      GO TO 98
      NPF=MAX(1,NPF-NPD/5)
      NPL=NPF+NPD
      GO TO 99
      NPL=MIN(NMAX,NPL+NPD/5)
      NPF=NPL-NPD
      GO TO 99
      DO 100 I=1,5
      IF(IX.LT.IXMIN(I).OR.IX.GT.IXMIN(I)+239)GO TO 100
      IF(IY.LT.IYMIN(I).OR.IY.GT.IYMIN(I)+239)GO TO 100
      ISTRIP=I
      GO TO 101
  100 CONTINUE
      GO TO 98
  101 XOFF=XMN(ISTRIP*2-1)+(IX-(IXMIN(ISTRIP)+1))*
     &     (XMX(ISTRIP*2-1)-XMN(ISTRIP*2-1))/238
      XZERO(ISTRIP*2-1)=XZERO(ISTRIP*2-1)+XOFF
      YOFF=XMN(ISTRIP*2)+(IY-(IYMIN(ISTRIP)+1))*
     &     (XMX(ISTRIP*2)-XMN(ISTRIP*2))/238
      XZERO(ISTRIP*2)=XZERO(ISTRIP*2)+YOFF
      ICHANGE(ISTRIP*2-1)=100
      ICHANGE(ISTRIP*2)=100
      GO TO 99
      CONTINUE
      GO TO 99
      CALL QUIT
      PRINT*,'DO YOU WANT TO QUIT [Y] '
      READ(5,'(A)')ANS
      IF(ANS.NE.'N'.AND.ANS.NE.'n')STOP
      CALL ENTGRA
      GO TO 98
      CALL MACRO(2)
      RETURN
      CALL READBUT(0,1,IBUT,IX,IYY)
      IY=MOD(IC+225-IYY,512)
      GO TO(1,2,3,4,5,6,7,8,9,10,11,12,13)IBUT
      CALL LISSAJOUS(ISTRIP,NPF,NPL)
      GO TO 98
      END
      FUNCTION LSTRING(STR)
      CHARACTER*(*) STR
      LL=LEN(STR)
      DO 1 II=1,LL
      I=LL+1-II
      IF(STR(I:I).NE." ".AND.STR(I:I).NE."<0>")GO TO 2
    1 I=0
    2 LSTRING=I
      RETURN
      END
      SUBROUTINE MENU_LISS
      CALL QUIT
      WRITE(5,100)
  100 FORMAT('1',T20,'TABLET FUNCTIONS FOR LISSOJOUS FIGURES'//
     &' BUTTON      FUNCTION'//
     &' GRAY    RETURN TO STRIP CHART      '/
     &' 1       DETERMINE ANGLE BETWEEN 2 POINTS '/
     &' 2       DECREASE LOCATION RANGE    '/
     &' 3       INCREASE LOCATION RANGE    '/
     &' 4       RESET    LOCATION RANGE    '/
     &' 5       DECREASE VALUE RANGE       '/
     &' 6       INCREASE VALUE RANGE       '/
     &' 7       COLOR PATTERN              '/
     &' 8       STEP BACKWARD IN LOCATION  '/
     &' 9       STEP FORWARD IN LOCATION   '/
     &' 0       SET ZERO FOR VALUE RANGE   '/
     &' *       REDRAW LISSAJOUS FIGURES   '/
     &' #       QUIT')
```

```
       CALL ENTGRA
       RETURN
       END
       SUBROUTINE MENU_STRIP
       CALL QUIT
       WRITE(6,100)
       FORMAT('1',T25,'TABLET FUNCTIONS FOR STRIP CHART'//
      ' BUTTON                         FUNCTIONS'/
      '        WHILE MOVING            WHEN STOPPED'//
      ' GRAY  PAUSE                    START MOVING'/
      '  1    REVERSE DIRECTION        REVERSE DIRECTION'/
      '  2    NO FUNCTION              DECREASE LOCATION RANGE  '/
      '  3    NO FUNCTION              INCREASE LOCATION RANGE  '/
      '  4    NO FUNCTION              RESET    LOCATION RANGE  '/
      '  5    NO FUNCTION              DECREASE VALUE RANGE     '/
      '  6    NO FUNCTION              INCREASE VALUE RANGE     '/
      '  7    NO FUNCTION              DRAW LISSAJOUS FIGURES'/
      '  8    NO FUNCTION              STEP BACKWARD IN LOCATION'/
      '  9    NO FUNCTION              STEP FORWARD IN LOCATION'/
      '  0    NO FUNCTION              SET ZERO FOR VALUE RANGE'/
      '  *    NO FUNCTION              PAUSE/UNPAUSE REDRAWING'/
      '  #                             QUIT')
       CALL ENTGRA
       RETURN
       END
       SUBROUTINE SPECT(P,IR,IG,IB)
       P1=P*14.
       P1=AMAX1(0.,AMIN1(14.,P1))
       P2=8-P1
       IF(P1.LT.4.)THEN
             IR=255-.784*P1**2-.05*P1**4
             IG=255-.784*P2**2-.05*P2**4
             IB=0
       ELSE IF(P1.LT.6.)THEN
             P1=4+(P1-4)*2
             P2=8-P1
             IR=255-.784*P1**2-.05*P1**4
             IG=255-.784*P2**2-.05*P2**4
             IB=0
       ELSE IF(P1.LT.8.)THEN
             P1=(P1-6)*4
             P2=8-P1
             P3=.75*P1
             IG=255-.784*P3**2-.05*P3**4
             IB=255-.784*P2**2-.05*P2**4
             IR=0
       ELSE IF(P1.LT.10.)THEN
             P1=(P1-8)*2
             P2=8-P1
             P3=6+P1
             IB=255-.784*P1**2-.05*P1**4
             IR=255-.784*P2**2-.05*P2**4
             IG=255-.784*P3**2-.05*P3**4
       ELSE
             P1=4+(P1-10)
             P2=8-P1
             IB=255-.784*P1**2-.05*P1**4
             IR=255-.784*P2**2-.05*P2**4
       ENDIF
       IR=MAX(0,MIN(255,IR))
       IG=MAX(0,MIN(255,IG))
       IB=MAX(0,MIN(255,IB))
       RETURN
       END
       SUBROUTINE LISS_SET
       COMMON/LISSAJOUS_RANGES/  IXMIN(5),IYMIN(5)
       CHARACTER*10 TITLE(5)
       DATA TITLE/'400 DIFF','100 DIFF','10 DIFF','MIX DIFF',
      &  'MIX DIFF'/
       CALL WRMASK(255,2)
       DO 1 I=1,4
       CALL VALB(128)
       CALL MOVABS(IXMIN(I),IYMIN(I))
       CALL RECREL(239,239)
       CALL MOVREL(0,120)
       CALL DRWREL(240,0)
       CALL MOVREL(-120,-120)
       CALL DRWREL(0,240)
       CALL MOVREL(-40,-10)
       CALL VALB(128)
       CALL TEXT1(10,TITLE(I))
   1   CONTINUE
       CALL MOVABS(-155,242)
       CALL CRIGHT
       CALL MOVABS(-253,226)
       CALL AILOGO
```

```
          CALL COLOR_STRIP_SET(TITLE,4)
          RETURN
          END
          SUBROUTINE READBUT(IT1,IT2,IBUT,IX,IY)
          CALL READBU(IT1,IT2,IBUT,IX,IY)
          IF(IBUT.EQ.0)RETURN
          CALL QUIT
          WRITE(6,100)CHAR(7)
          FORMAT("+",A1)
          CALL ENTGRA
          RETURN
          END
          SUBROUTINE AILOGO
          SAVE IP1,IP2
          DIMENSION IP1(22),IP2(34)
          DATA IP1/15,24,11,21,2,2,0,1,0,0,6,0,11,3,5,3,5,4,6,5,7,5/
          DATA IP2/10,7,11,9,12,9,19,9,21,6,21,5,20,5,20,4,20,3,28,3,23,0,
        &          14,0,14,1,15,1,15,2,14,6,14,7/
          CALL CMOVE(60,0)
          CALL PRMFIL(1)
          CALL POLYGN(1,11,IP1)
          CALL POLYGN(1,17,IP2)
          CALL MOVREL(15,13)
          CALL CIRCLE(2)
          CALL PRMFIL(0)
          CALL CMOVE(0,60)
          RETURN
          END
          SUBROUTINE CRIGHT
          CALL CMOVE(60,0)
          CALL MOVREL(5,3)
          CALL CIRCLE(5)
          CALL ARC(3,45,315)
          CALL MOVREL(10,-3)
          CALL TEXT1(48,
        & "Copyright 1984 Westinghouse Electric Corporation")
          CALL CMOVE(0,60)
          RETURN
          END
```

I claim:

1. A method for producing a display of eddy current test data from signals produced by an eddy current detector which is supplied with an alternating current signal composed of alternating currents at several different frequencies, the detector signals including a respective signal associated with each alternating current and varying in amplitude and in phase relative to its associated alternating current as the detector is displaced along a selected path relative to a test body, comprising:

generating, from each detector signal, a data signal representing the detector signal component in phase with the alternating current associated with that detector signal and a data signal representing the detector signal component in quadrature with the alternating current associated with that detector signal;

storing a representation of each data signal; and supplying the representation of each data signal to a display device for producing a first display composed of visible representations of all data signals along parallel reference axes, with each reference axis being associated with a respective data signal and being representative of the selected path of movement of the detector relative to the test body.

2. A method as defined in claim 1 further comprising varying the scale of a selected visible representation in the direction of the reference axis associated with that visible representation.

3. A method as defined in claim 1 further comprising varying the scale of a selected visible representation in the direction perpendicular to the reference axis associated with that visible representation.

4. A method as defined in claim 1 further comprising varying the position of a selected visible representation relative to the reference axis associated with that visible representation.

5. A method as defined in claim 1 further comprising selecting end points of a visible representation of a data signal representing one component of a detector signal along the reference axis associated with that representation, and producing a second display constituting a visible representation of the ratio of the value of that data signal to the value of the data signal representing the other component of the same detector signal, for signal values between the selected end points.

6. Apparatus for producing a display of eddy current test data from signals produced by an eddy current detector which is supplied with an alternating current signal composed of alternating currents at several different frequencies, the detector signals including a respective signal associated with each alternating current and varying in amplitude and in phase relative to its associated alternating current as the detector is displaced along a selected path relative to a test body, comprising:

means for storing, with respect to each detector signal, a representation of a data signal representing the detector signal component in phase with the alternating current associated with that detector signal and a representation of a data signal representing the detector signal component in quadrature with the alternating current associated with that detector signal; and display means connected to said means for storing for receiving each data signal representation and for producing a first display composed of representations of all data signals along parallel reference axes, with each reference axis being associated with a respective data signal and being representative of the selected path of movement of the detector relative to the test body.

7. Apparatus as defined in claim 6 further comprising interactive, operator actuated display control means connected to said display means and operable for effecting selection of end points of a visible representation of a data signal representing one component of a detector signal along the reference axis associated with that representation, and means for producing a second display constituting a visible representation of the ratio of the value of the data signal to the value of the data signal representative of the other component of the same detector signal, for signal values between the selected end points.

8. A method as defined in claim 1 wherein the display device is a color display device and said step of supplying is carried out for causing the visible representation of each data signal of said first display to have a respectively different color.

9. Apparatus as defined in claim 6 wherein said display means comprise a color display device and said means for storing supply to said display means data signal representations for causing the visible representation of each data signal of said first display to have a respectively different color.

* * * * *